(12) United States Patent
Epstein et al.

(10) Patent No.: US 10,470,838 B2
(45) Date of Patent: Nov. 12, 2019

(54) SURGICAL SYSTEM FOR SPATIAL REGISTRATION VERIFICATION OF ANATOMICAL REGION

(71) Applicant: MAKO Surgical Corp., Fort Lauderdale, FL (US)

(72) Inventors: Danielle Epstein, Fort Lauderdale, FL (US); Carinne Granchi, Fort Lauderdale, FL (US)

(73) Assignee: MAKO Surgical Corp., Fort Lauderdale, FL (US)

(*) Notice: Subject to any disclaimer, the term of this patent is extended or adjusted under 35 U.S.C. 154(b) by 1198 days.

(21) Appl. No.: 14/136,499

(22) Filed: Dec. 20, 2013

(65) Prior Publication Data

US 2014/0206990 A1 Jul. 24, 2014

Related U.S. Application Data

(60) Provisional application No. 61/740,984, filed on Dec. 21, 2012.

(51) Int. Cl.
| | |
|---|---|
| *A61B 90/00* | (2016.01) |
| *A61B 6/03* | (2006.01) |
| *A61B 6/12* | (2006.01) |
| *A61B 5/11* | (2006.01) |
| *A61B 34/20* | (2016.01) |
| *A61B 5/00* | (2006.01) |
| *A61B 5/06* | (2006.01) |
| *A61B 34/10* | (2016.01) |

(52) U.S. Cl.
CPC ............ *A61B 90/37* (2016.02); *A61B 5/1116* (2013.01); *A61B 5/1127* (2013.01); *A61B 6/032* (2013.01); *A61B 6/12* (2013.01); *A61B 34/20* (2016.02); *A61B 5/0037* (2013.01); *A61B 5/066* (2013.01); *A61B 5/4504* (2013.01); *A61B 5/7425* (2013.01); *A61B 5/7475* (2013.01); *A61B 2034/104* (2016.02); *A61B 2034/2055* (2016.02)

(58) Field of Classification Search
CPC ........ A61B 5/1077; A61B 6/032; A61B 19/50
See application file for complete search history.

(56) References Cited

U.S. PATENT DOCUMENTS

| | | | | |
|---|---|---|---|---|
| 2006/0184029 | A1* | 8/2006 | Haim | A61B 5/02007 600/443 |
| 2008/0123910 | A1* | 5/2008 | Zhu | A61B 90/36 382/128 |
| 2009/0221908 | A1* | 9/2009 | Glossop | A61B 17/3403 600/424 |

* cited by examiner

*Primary Examiner* — Joseph M Santos Rodriguez
(74) *Attorney, Agent, or Firm* — Foley & Lardner LLP

(57) ABSTRACT

A method for verifying a spatial registration of an anatomical region is provided. The method may track a spatial pose of at least one checkpoint defined within the anatomical region, track a spatial pose of a probe tip in proximity to the anatomical region at the checkpoint, map a spatial proximity between the probe tip and the anatomical region onto a visual representation of the anatomical region based on the tracked spatial poses, quantify a deviation between the mapped spatial proximity and an actual spatial proximity in response to a verification request where the verification request is initiated by a user and indicative of the actual spatial proximity between the probe tip and the anatomical region, and generate a graphical index indicative of a degree of accuracy of the spatial registration of the anatomical region based on the quantified deviation.

22 Claims, 8 Drawing Sheets

SURGICAL SYSTEM FOR SPATIAL REGISTRATION VERIFICATION OF ANATOMICAL REGION

CROSS-REFERENCE TO RELATED APPLICATION

This is a non-provisional application claiming priority under 35 USC § 119(e) to US Provisional Patent Application Ser. No. 61/740,984 filed on Dec. 21, 2012.

TECHNICAL FIELD

The present disclosure generally relates to surgical systems, and more particularly, to systems and methods for computer-aided surgical planning and procedures.

BACKGROUND

A surgeon performing an orthopedic procedure is met with a variety of obstacles due to the limited visibility and access to a diseased anatomical region of interest. Often, surgeons will rely on computer-aided or robot-guided systems to help them more intuitively plan for the surgical procedures at hand. Computer-aided systems generally enable surgeons to graphically model an anatomical region using medical images, such as computer tomography (CT) scans, and the like. Once a plan or model is generated, the surgeon may then view the model on a display screen in the operating room as guidance while performing the actual tasks. Such computer-aided systems have become a valuable tool in the operating room, especially in applications involving anatomical regions that are particularly difficult to access, where the surgeon must often rely solely or mostly on the graphical models for guidance.

Much of the reliability of computer-aided surgical systems rests upon the means by which it is first configured or calibrated for accuracy. Prior to implementation, it is common to register certain geometric features of a particular anatomic region or structure to a graphical representation or model of the structure for display and manipulation by a user. The registration process helps synchronize the actual geometry of the anatomical structure, as well its spatial position and/or orientation of the structure relative to the surgical environment, with the modeled structure. Although such registration steps help improve the accuracy of the model, any subsequent change, offset or shift to the pose of the actual structure that may be untracked by the computer-aided system can compound errors during a surgical task.

Accordingly, there is a need for improved systems or methods that provide facilitated means for verifying a spatial registration of an anatomical region of interest prior to or during a surgical procedure. In particular, there is a need for a system or method that can improve the reliability of computer-aided surgical procedures by enabling more accurate and more consistent modeling of an anatomical region throughout the surgical process.

SUMMARY OF THE DISCLOSURE

In one aspect of the present disclosure, a method for verifying a spatial registration of an anatomical region is provided. The method may track a spatial pose of at least one checkpoint defined within the anatomical region, track a spatial pose of a probe tip in proximity to the anatomical region at the checkpoint, map a spatial proximity between the probe tip and the anatomical region onto a visual representation of the anatomical region based on the tracked spatial poses, quantify a deviation between the mapped spatial proximity and an actual spatial proximity in response to a verification request where the verification request is initiated by a user and indicative of the actual spatial proximity between the probe tip and the anatomical region, and generate a graphical index indicative of a degree of accuracy of the spatial registration of the anatomical region based on the quantified deviation.

In another aspect of the disclosure, a method for verifying a spatial registration of an anatomical region is provided. The method may track a spatial relationship between a probe tip and the anatomical region at a checkpoint defined within the anatomical region, generate a graphical user interface based on the tracked spatial relationship between the probe tip and the anatomical region, receive a verification request that is initiated by a user and received through the graphical user interface, where the verification request is indicative of an actual contact between the probe tip and the anatomical region, determine the accuracy of the spatial registration of the anatomical region based on any deviation between the tracked spatial relationship of the probe tip relative to the anatomical region and the actual contact as indicated by the user, and generate a graphical index within the graphical user interface indicative of the accuracy of the spatial registration.

In yet another aspect of the disclosure, a system for verifying a spatial registration of an anatomical region is provided. The system may include a probe having a probe tip disposed at a distal end thereof, a tracking device configured to track a spatial proximity of the probe tip relative to the anatomical region at a checkpoint defined within the anatomical region, and a computing device in communication with at least the tracking device. The computing device may include an input device, an output device, a memory, and at least one controller. The controller may be configured to map the spatial proximity between the probe tip and the anatomical region onto a visual representation of the anatomical region based on tracking information provided by the tracking device, receive a verification request through the input device that is indicative of an actual spatial proximity between the probe tip and the anatomical region, quantify a deviation between the mapped spatial proximity and the actual spatial proximity in response to the verification request, and display a graphical index on the output device that is indicative of a degree of accuracy of the spatial registration of the anatomical region based on the quantified deviation.

DETAILED DESCRIPTION

Reference will now be made in detail to specific embodiments or features, examples of which are illustrated in the accompanying drawings. Generally, corresponding reference numbers will be used throughout the drawings to refer to the same or corresponding parts. Although the following disclosure may make certain references to orthopedic procedures, it should be understood that the subject matter described herein may be used in association with other applicable procedures.

Figure 1:
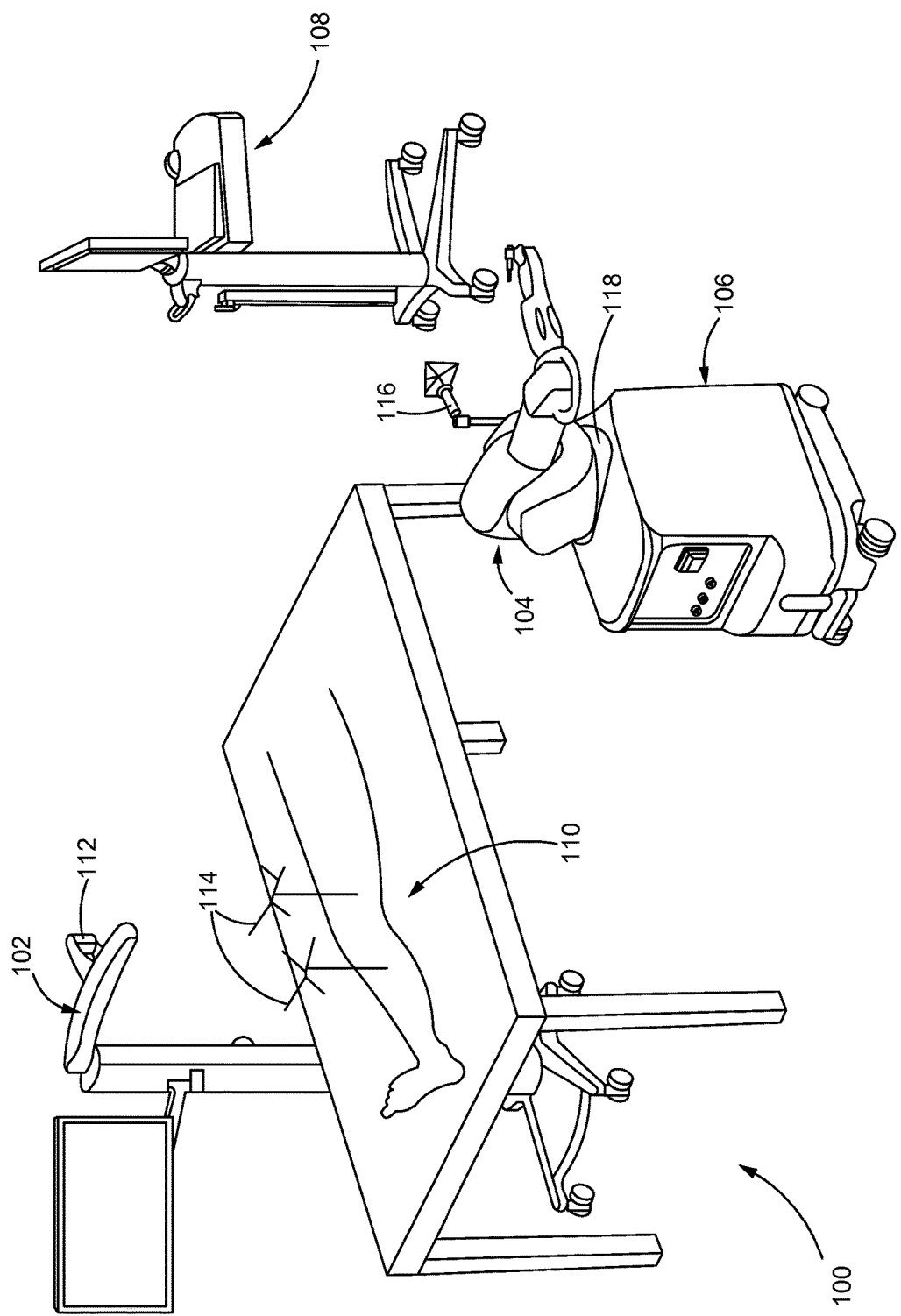
FIG. 1 is a graphical view of one exemplary embodiment of a surgical system configured to verify a spatial registration of an anatomical region.

Referring to FIG. 1, one exemplary embodiment of a surgical system 100 is provided. As shown, the surgical system 100 may generally include a tracking device 102, a controllable surgical device 104, a computing device 106 associated with each of the tracking and surgical devices 102, 104, as well as a user interface 108 for interfacing with the computing device 106. The tracking device 102 may track any changes to the position and/or orientation of an anatomical region of interest 110 as well as the movement, position and/or orientation of the controllable surgical device 104 or a tool thereof. The computing device 106 may graphically process the tracked movements, positions and/or orientations of the surgical device 104 relative to the anatomical region 110 into visual representations or models to be viewed and/or manipulated by a user, such as a surgeon or other qualified personnel, via the user interface 108 while planning or performing a surgical procedure.

The tracking device 102 of FIG. 1 may further include means for tracking movement of the anatomical region of interest 110. In particular, the tracking device 102 may employ one or more detectors 112 to spatially track one or more spatially detectable markers 114 that are disposed near the anatomical region 110. As shown, the markers 114 may be fixedly attached to appropriate and relevant sections of the anatomical region 110 so as to enable monitoring and tracking of any changes in the spatial pose of the anatomical region 110, for example, in terms of translations, tilts, and the like, which may occur during a surgical procedure or during preparations therefor. The markers 114 may further include one or more detectable arrays of pins, screws, or the like, disposed within or about the anatomical region 110, such as for bone structures, to enable monitoring and tracking of any changes in the spatial pose thereof. As used herein, "pose" means position and/or orientation.

The tracking device 102 may similarly include means for tracking a spatial pose of a marker 116 associated with the controllable surgical device 104 so as to track the spatial pose of the surgical device 104 in relation to the anatomical region 110. For example, the tracking device 102 may be configured to track specific unique identifiers that are associated with the surgical device 104, or a working end or tool thereof, so as to distinguish the marker 116 of the surgical device 104 from the markers 114 associated with the anatomical region 110. Alternatively, information provided by the tracking device 102 may be used in conjunction with a net displacement of the surgical device 104 as detected from within a base 118 thereof or by the computing device 106 associated therewith. Based on the net displacement sensed, the spatial pose of the surgical device 104, or a tool attached thereto, may be tracked relative to the base 118 as well as the anatomical region 110. By simultaneously tracking the distinct markers 114, 116, and in conjunction with any other information made available by the surgical device 104, the tracking device 102 may be able to provide substantially live feedback pertaining to the relative spatial movements, positions and/or orientations between the surgical device 104, or a tool thereof, and the anatomical region 110.

Figure 2:
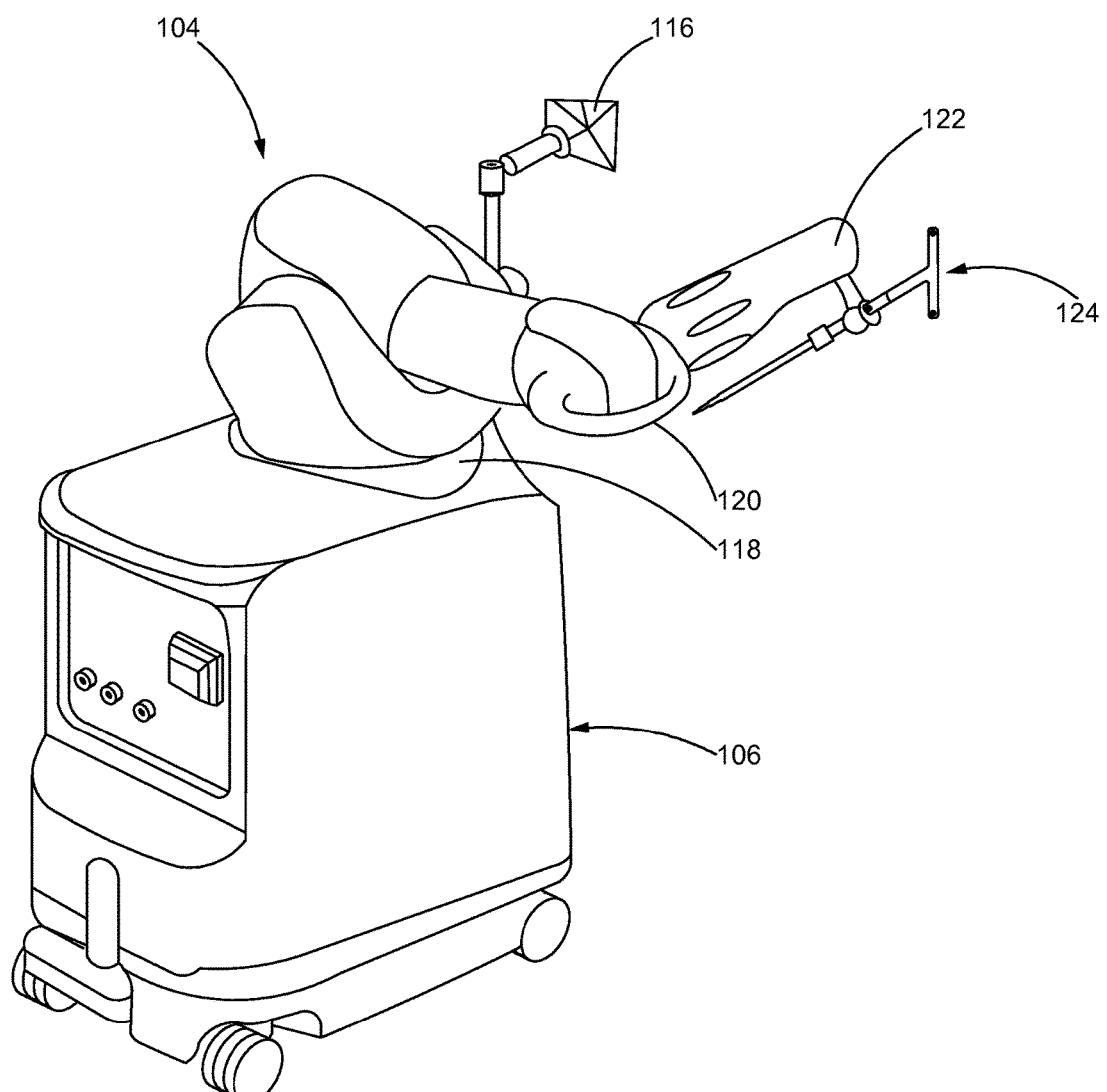
FIG. 2 is a perspective view of one exemplary embodiment of a controllable surgical device configured to verify a spatial registration of an anatomical region.

Turning to FIG. 2, the controllable surgical device 104 may include a robotic device, such as an articulated arm 120, or the like, that is at least partially monitored and/or controlled by the computing device 106. The articulated arm 120 may be anchored to the base 118 and provided with a working end 122 to which the distal end of a surgical tool, such as a probe 124, may be removably coupled. The spatial pose of the probe 124 may be manipulated by grasping and manually moving the articulated arm 120 of FIG. 2 relative to its base 118. Optionally, the spatial pose of the probe 124 and thus movement of the articulated arm 120 may be facilitated or manipulated through instructions that may be provided by a user through the user interface 108 and processed into motor control signals by the computing device 106. The articulated arm 120 may also be provided with a force feedback mechanism, or the like, that may be operated by the computing device 106 and configured to guide or limit manual manipulation of the probe 124 and the attached articulated arm 120.

Figure 3:
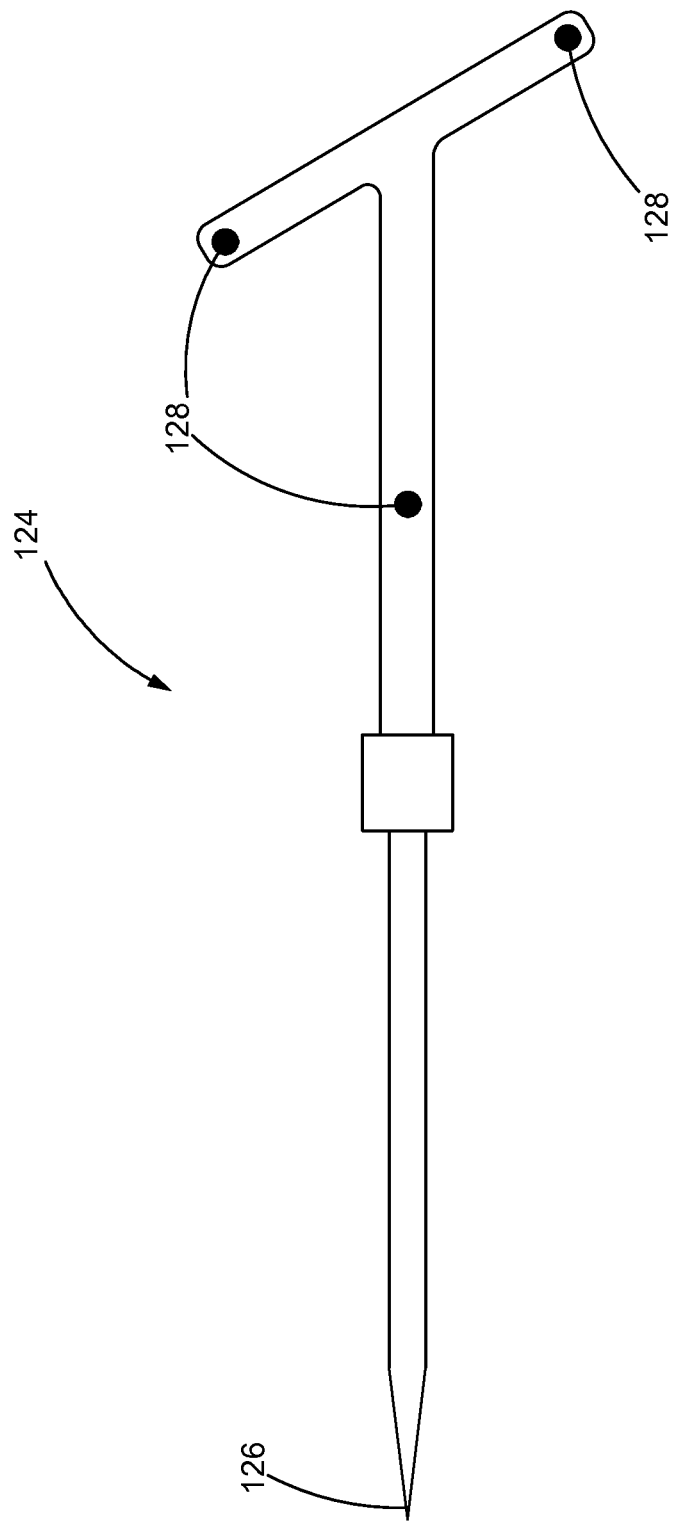
FIG. 3 is a side plan view of one exemplary detectable probe that can be used in conjunction with a controllable surgical device.

Additionally, as further shown in FIG. 3, the probe 124 may include a probe tip 126 that is disposed at a distal end thereof, as well as an array of detectable markers 128 that is generally disposed at a proximal end thereof. More specifically, the markers 128 may be configured to be detectable by the detectors 112 of the tracking device 102, and positioned in such a way as to enable the tracking device 102 to at least partially track the spatial pose of the probe 124 and the probe tip 126 during a surgical procedure. Among other things, the probe 124 may be used in part for the purposes of, for example, registering and/or verifying an anatomical region 110, such as a bone structure, or the like, during a surgical planning stage and prior to a surgical procedure. A registration process may generally serve to map actual spatial relationships between the surgical device 104 and the anatomical region 110 onto visual representations or models which may be viewed and manipulated by a user via the user interface 108. Moreover, the visual representations may be derived in part based on tracking information provided by the tracking device 102. A verification process may generally serve to ensure that the spatial relationships between the surgical device 104 and the anatomical region 110, as tracked and mapped during the registration process, accurately corresponds to and is in sufficient agreement with actual spatial relationships therebetween.

Figure 4:
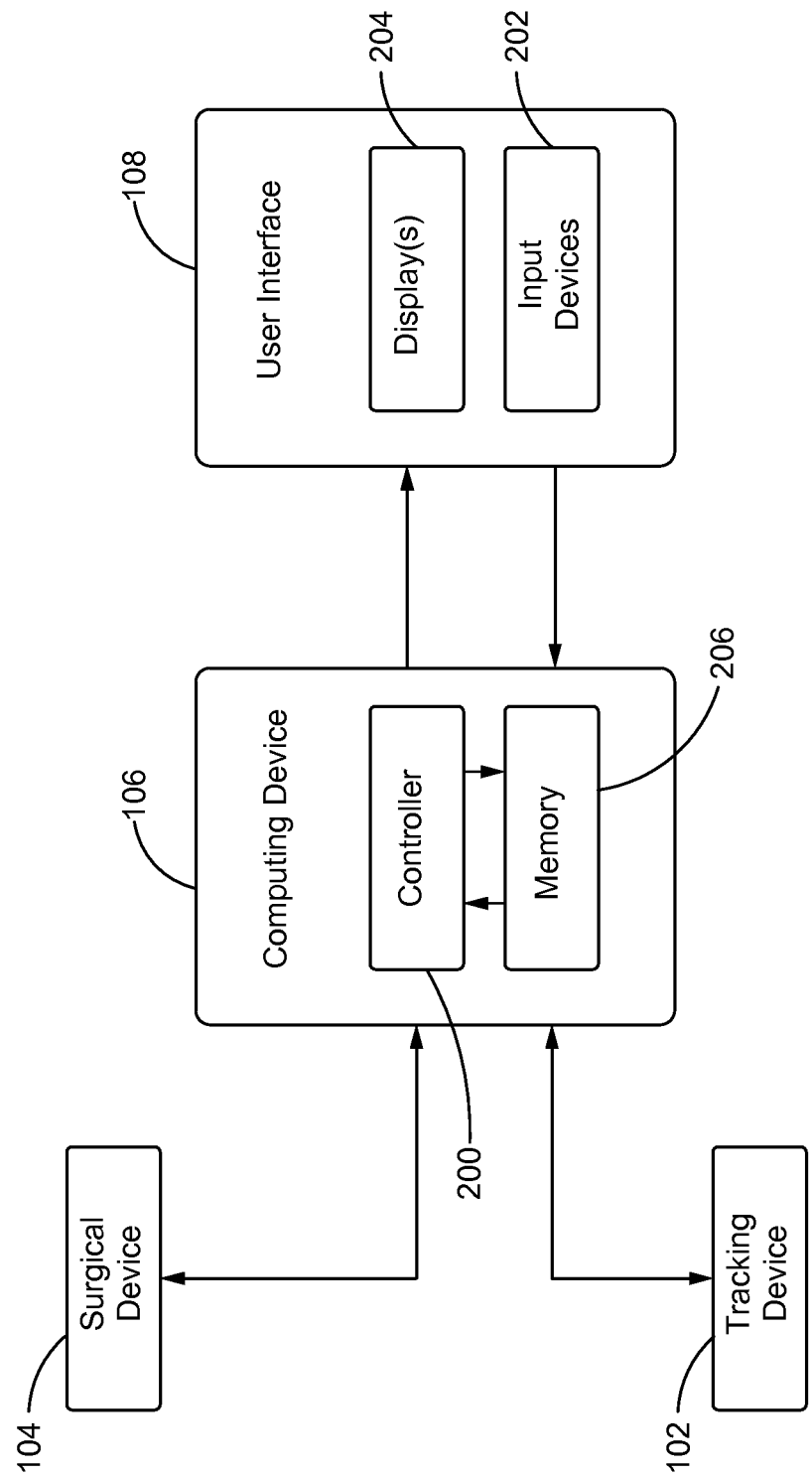
FIG. 4 is a schematic view of one exemplary computing device configured to verify a spatial registration of an anatomical region.

Registration and/or verification processes may generally be performed and facilitated by the computing device 106, as schematically illustrated in FIG. 4. For example, the computing device 106 may include hardware and software configured to continuously guide the surgeon through a bone registration process, a bone verification process, or any other related procedures. As shown, the computing device 106 may include one or more controllers 200 that are in wired or wireless communication with the tracking device 102, the surgical device 104, as well as any input devices 202 and output or display devices 204 associated with the user interface 108. The controller 200 may be implemented using any one or more of a processor, a microprocessor, a microcontroller, a field programmable gate array (FPGA), or any other suitable programmable means for controlling the computing device 106.

Still referring to the embodiment of FIG. 4, the input device 202 may include any one or more of a keyboard, a mouse, a trackball, a touch screen, a touch pad, a microphone, a dial, a switch, a button, a camera, or any other suitable device enabling input by a user. The display device 204 may include a liquid crystal display (LCD), a cathode ray tube (CRT) display, a plasma screen, a touch screen, and/or any other suitable output device for displaying a graphical user interface to a user. The computing device 106 may further include memory 206 for at least temporarily storing one or more medical images of the anatomical region 110 as obtained by computer tomography (CT) devices, magnetic resonance imaging (MRI) devices, fluoroscopic devices, ultrasound devices, and the like. Based on the medical images, the controller 200 may be able to construct two- or three-dimensional visual representations or models of the anatomical region 110, which may be viewed and/or manipulated by a user via the input and output devices 202, 204. The memory 206 may further be used to store one or more algorithms by which the controller 200 and the computing device 106 may be configured to operate.

Figure 5:
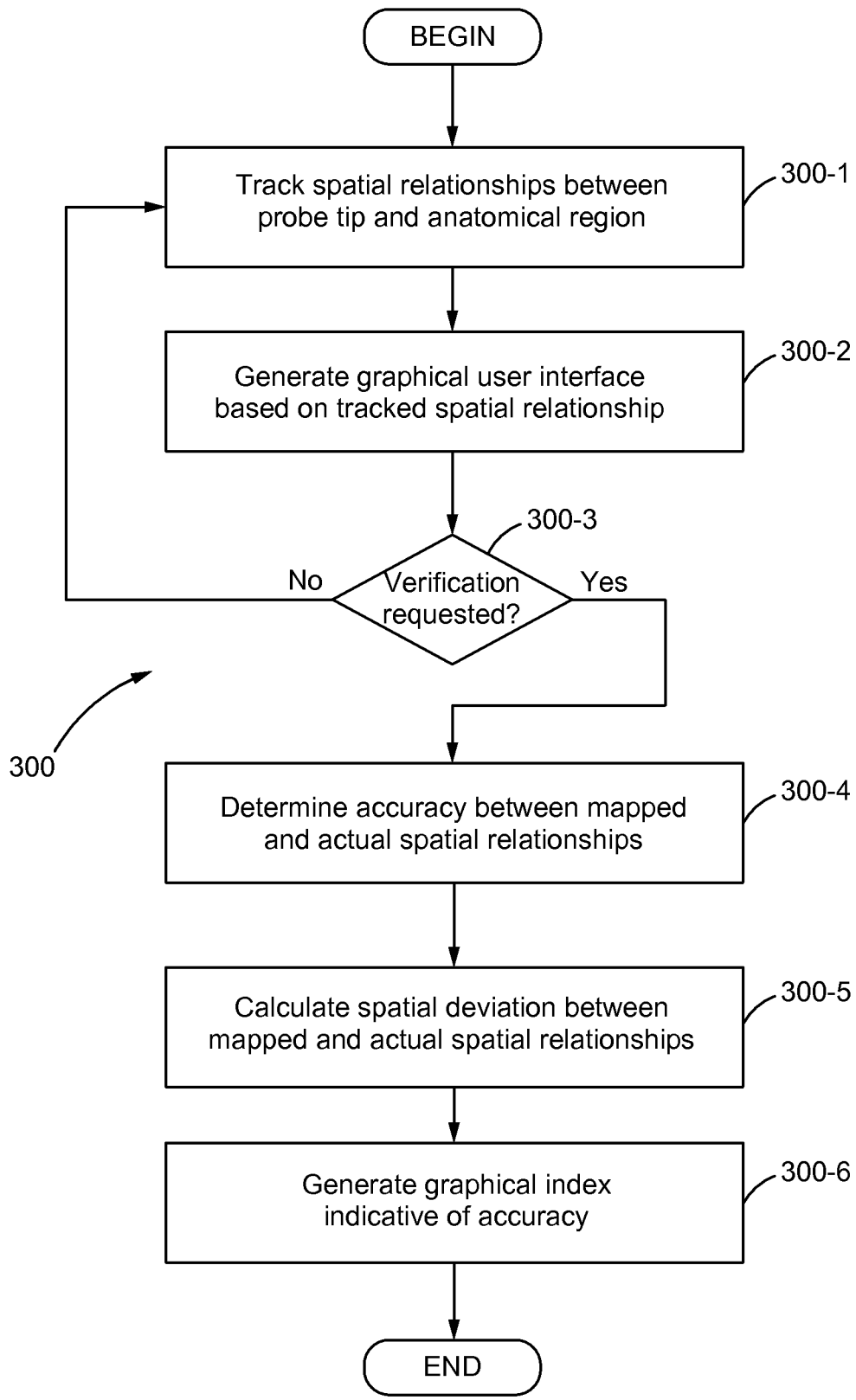
FIG. 5 is a diagrammatic view of one exemplary method for verifying a spatial registration of an anatomical region.

Turning to the embodiment of FIG. 5, one exemplary algorithm or method 300 by which the controller 200 of the computing device 106 may be configured to perform a registration process is provided. Specifically, the method 300 may be preprogrammed, in the form of executable code, onto a memory 206 that is accessible to the controller 200 to operate the computing device 106 according to one or more of the steps shown. As shown in FIG. 5, in step 300-1, the controller 200 may be configured to track the spatial relationships between the surgical device 104 and the anatomical region 110. More specifically, the controller 200 may track the spatial pose of the probe tip 126, the distal end of which is coupled to the working end 122 of the surgical device 104, in relation to the spatial pose of a surface of the anatomical region of interest 110.

The controller 200 may track the spatial pose of the probe 124 and the probe tip 126 by employing the tracking device 102 to directly track the array of markers 128 on the body of the probe 124. The controller 200 may alternatively derive the spatial pose of the probe tip 126 by tracking the marker 116 associated with an articulated arm 120 of the surgical device 104 and applying known geometric relationships between the probe 124 and the working end 122 of the articulated arm 120. In still further alternatives, the controller 200 may derive the spatial pose of the probe tip 126 based in part on a net spatial displacement detected within the controllable articulated arm 120. Furthermore, in order to track the spatial pose of the anatomical region 110, the controller 200 may employ tracking information from the tracking device 102 relating to detection of an array of anatomical checkpoints 130 disposed within or on the anatomical region 110. The controller 200 may alternatively track the spatial relationship between the surgical device 104 and the anatomical region 110 using any other suitable means commonly used in the art.

Figure 6:
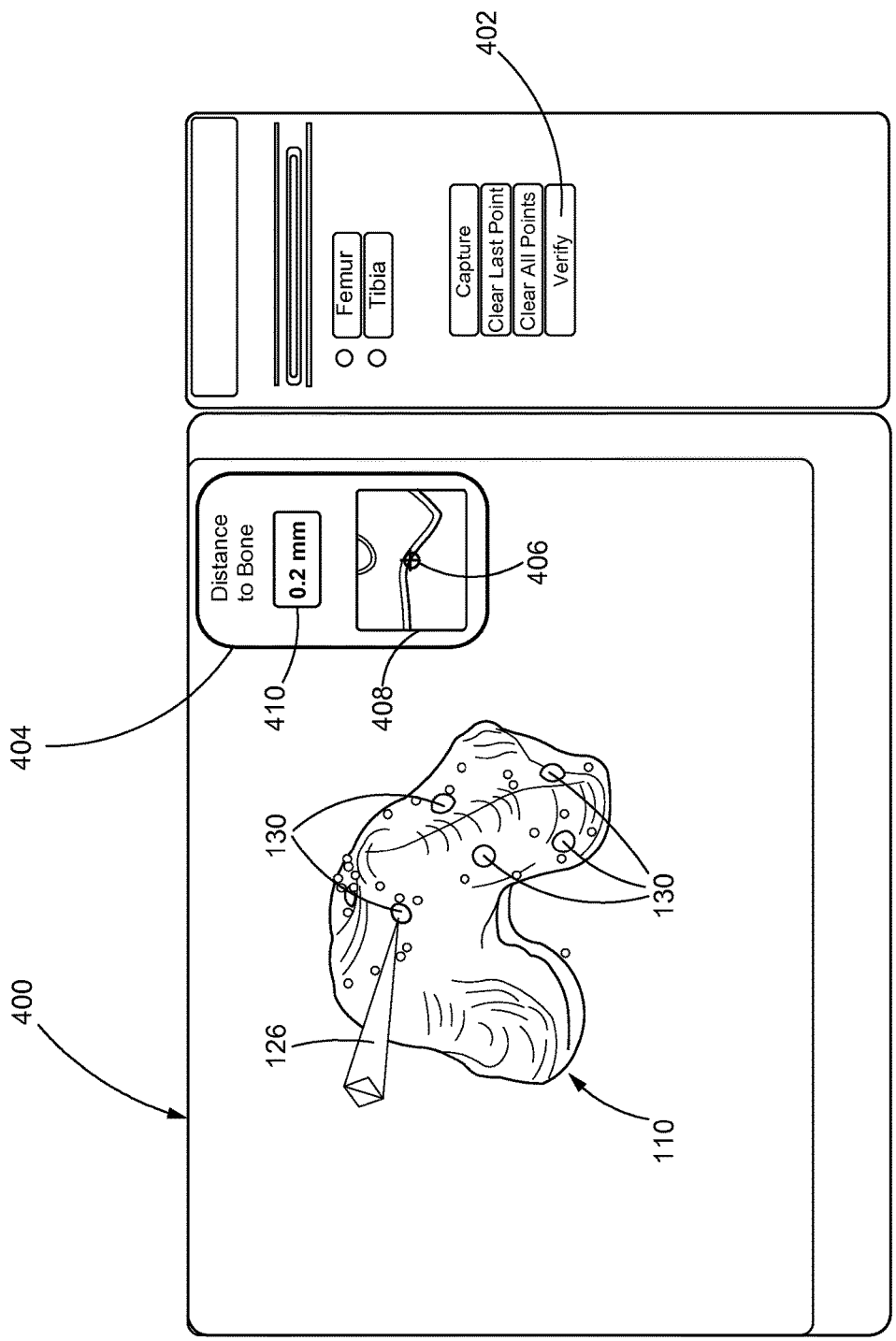
FIG. 6 is a graphical view of one exemplary graphical user interface having a graphical accuracy index as provided by the present disclosure.

In step 300-2, the controller 200 may be configured to generate or maintain a graphical user interface based on the spatial relationships tracked in step 300-1. As shown in FIG. 6, for example, the graphical user interface 400 may provide a visual representation or model of the anatomical region of interest 110 to be presented to a user via one or more of the output or display devices 204 associated with the computing device 106. The visual representation or model may be generated in part using one or more medical images of the actual anatomical region 110 as captured, for example, using CT devices, MRI devices, fluoroscopic devices, ultrasound devices, and the like. More specifically, the controller 200 may obtain tracking information provided by the tracking device 102, and superimpose or spatially map the tracking information onto one or more of the medical images so as to construct two- or three-dimensional models to be displayed within the graphical user interface 400. The resulting visual representations of the probe tip 126 and the anatomical region 110, as well as the spatial poses thereof, may substantially correspond to the actual position and orientation of the probe tip 126 relative to the anatomical region 110. Using one or more of the input devices 202, the user may be able to manipulate the models or adjust views thereof from within the graphical user interface 400. Alternatively, the controller 200 may be configured to automatically adjust, select or present the viewing plane which best facilitates visualization of the probe tip 126 in relation to the anatomical region 110 or checkpoints 130 thereof.

Figure 7:
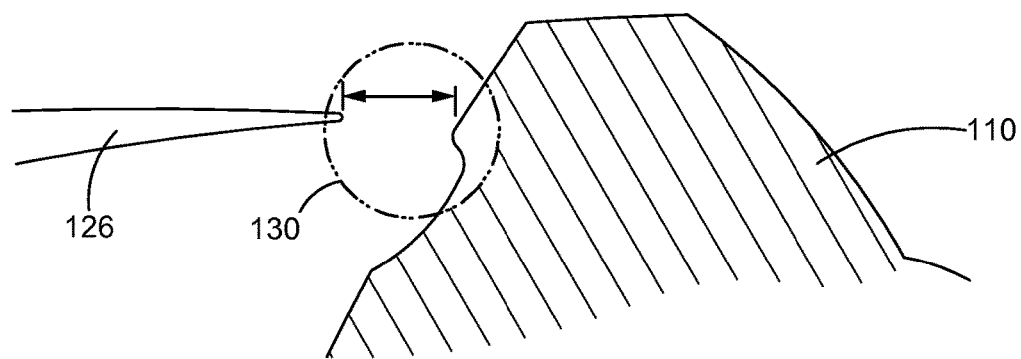
FIG. 7 is an illustrative view of a probe tip being placed in proximity to a checkpoint.

While viewing the graphical user interface 400, there may be some uncertainty as to the accuracy of the spatial registration of the surgical device 104 as well as the anatomical region 110 displayed. Accordingly, the graphical user interface 400 may provide a verification feature 402, for example, the "Verify" button shown in FIG. 6, which a user may use to verify the accuracy of the mapped spatial relationship prior to performing a surgical procedure. More specifically, as shown in FIG. 7 for example, the user may first manually position the probe tip 126 so as to approach a surface of the anatomical region 110 at one of the checkpoints 130 and within the spherical zone defined by the checkpoint 130. When actual contact is made between the probe tip 126 and the surface of the anatomical region 110 from within the selected checkpoint 130, the user may, for example, select the "Verify" option 402 to request verification of the accuracy of the spatial registration between the probe tip 126 and the surface of the anatomical region 110. As shown in step 300-3 of FIG. 5, if such a verification request 402 is received through the graphical user interface 400, the controller 200 may be configured to proceed to determine the accuracy of or any deviation in the spatial registration. If no such verification request 402 is received during step 300-3, the controller 200 may simply continue to track the probe tip 126 and the anatomical region 110 and update the graphical user interface 400 accordingly.

Once a verification request 402 is received, the controller 200 may be configured to determine the accuracy or the degree of agreement between the mapped and the actual spatial relationships between the probe tip 126 and an underlying surface of the anatomical region 110 at a checkpoint 130 in step 300-4. In general, the verification request 402 may be an inherent indication by the user initiating the verification that actual contact exists between the point tip 126 and the anatomical region 110 at the checkpoint 130 in question. Using this as reference, the controller 200 may determine if the tracked and thus mapped spatial relationship also agreeably indicates a perceived contact between the probe tip 126 and the anatomical region 110. For example, if the controller 200 finds a notable or significant spatial deviation in the mapped proximity between the probe tip 126 and the anatomical region 110 as derived via tracking information, as compared to the actual proximity (or the actual contact) therebetween, the controller 200 may indicate such a deviation through the graphical user interface 400. Alternatively, if the controller 200 determines there is no substantial deviation between the mapped proximity of the probe tip 126 relative to the anatomical region 110 at the selected checkpoint 130 and the actual proximity (or the actual contact) therebetween, the controller 200 may indicate such a verification of the agreement for at least that checkpoint 130. Furthermore, the minimal spatial deviation that is permitted between mapped and actual spatial relationships may be a predefined or a user-specified threshold that is stored within a memory 206 that is accessible to the controller 200.

In furtherance to step 300-4, if a significant spatial deviation is determined, the controller 200 may additionally quantify or calculate the deviation as indicated in step 300-5 of FIG. 5. More particularly, the controller 200 may be configured to measure the perceived distance between the mapped positions of the probe tip 126 and the anatomical region 110. This perceived distance may directly correspond to the calculated deviation between the mapped and actual spatial relationships of the probe tip 126 and the anatomical region 110 as long as the verification request 402 that is initiated by the user also indicates an actual contact between the probe tip 126 and the anatomical region 110 that is maintained by the user. Furthermore, the perceived distance between the probe tip 126 and the anatomical region 110 may be measured based on a two-axis, three-axis, six-axis, or any other suitable multi-axis coordinate system, and further, may provide approximate resolutions of a few hundredths or a few thousandths of a millimeter.

Figure 8:
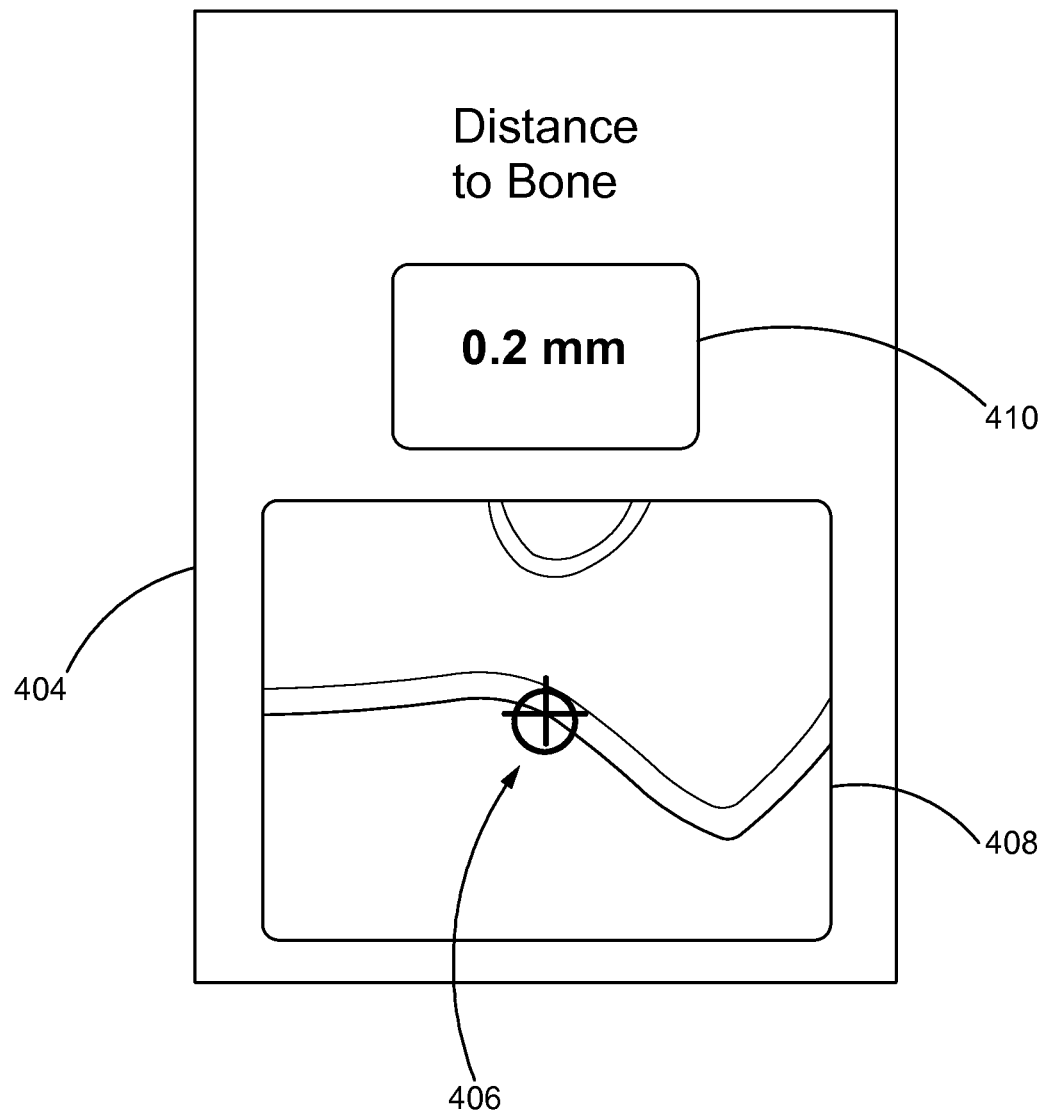
FIG. 8 is a graphical view of one exemplary graphical index as provided by the present disclosure.

In addition, the controller 200 in step 300-6 may be configured to generate a graphical index 404, as shown for example in FIG. 6 as well as in FIG. 8, which may provide a more detailed indication of the accuracy between the mapped and actual spatial relationships. More specifically, the graphical index 404 may provide a detailed cross-sectional view 408 of the relevant region of interest in relation to the tracked spatial position of the probe tip 126, which can further guide the user during verification or manipulation of the spatial position of the probe tip 126. Additionally, the view 408 of the anatomical region 110 displayed within the graphical index 404 may employ actual, two-dimensional graphical images of the anatomical region 110 at the relevant locations as provided by any one of a plurality of appropriate imaging devices. For example, in generating the view 408 within the graphical index 404 of FIG. 8, the controller 200 may refer to a set of CT images previously collected and stored within a database that is accessible to the controller 200. In particular, each CT image or cross-sectional view 408 of the anatomical region 110 may be indexable such that the controller 200 is able to retrieve and display the appropriate cross-sectional views of the anatomical region 110 based on the tracked spatial position or pose of the probe tip 126. Furthermore, the controller 200 may be adapted to continuously, in real time, or at a substantially high refresh rate, update the CT view 408 that is displayed to the user by indexing and retrieving new CT images or cross-sectional views in response to any detected changes in the spatial pose of the probe tip 126 relative to the anatomical region 110.

The graphical index 404 as shown in FIG. 8 may also provide a crosshair indicator 406 that is superimposed on the cross-sectional view 408, or CT image, of the anatomical region 110 to graphically indicate the perceived location of the probe tip 126 and to further aid the user in manipulating and verifying the spatial position of the probe tip 126 in relation to the surface of the anatomical region 110. The dimensions of the crosshair 406 may be fixed or predefined according to a desired resolution of accuracy. The crosshair indicator 406 may also change shape, change color, change size, or the like, according to the proximity of the probe tip 126 relative to the surface of the anatomical region 110. For each checkpoint 130 of the anatomical region 110 which undergoes a verification session, the graphical index 404 may also provide a numeric view 410 to numerically indicate the accuracy, or the distance of deviation, between the actual proximity of the probe tip 126 relative to the anatomical region 110 as compared with the perceived proximity as mapped. In other modifications, the graphical index 404 may employ combinations of a numerical index, a color-coded index, and any other suitable index, to indicate the accuracy of the mapped spatial relationships between the probe tip 126 and the surfaces of the anatomical region 110.

While only certain embodiments have been set forth for the purposes of illustration, alternatives and modifications will be apparent from the above description to those skilled in the art. These and other alternatives are considered equivalents and within the spirit and scope of this disclosure and the appended claims.

What is claimed is:

1. A method for verifying an accuracy of a tracked spatial relationship between a robotic device and an anatomical region relative to an actual spatial relationship therebetween, comprising the steps of:
    tracking identifiers associated with first markers to determine a spatial pose of at least one checkpoint defined within the anatomical region;
    tracking identifiers associated with second markers to determine a spatial pose of a probe tip of a probe held by the robotic device when the probe tip is in proximity to the anatomical region at the checkpoint;
    mapping a tracked spatial proximity between the probe tip and the anatomical region onto a visual representation of the anatomical region based on the tracked spatial poses;
    quantifying a deviation between the tracked spatial proximity and an actual spatial proximity in response to a verification request, the verification request being initiated by a user via a graphical user interface and being indicative of the actual spatial proximity between the probe tip and the anatomical region; and
    generating a graphical index on the graphical user interface indicative of a degree of accuracy of the tracked spatial relationship between the robotic device and the anatomical region relative to the actual spatial relationship based on the deviation.

2. The method of claim 1, wherein the verification request is indicative of actual contact between the probe tip and the anatomical region.

3. The method of claim 1, wherein the checkpoint is defined as one of a marker, a pin, and a screw that is detectable by a tracking device.

4. The method of claim 1, wherein the visual representation is based on at least one medical image.

5. The method of claim 4, wherein the medical image includes a computer tomography (CT) scan of the anatomical region.

6. The method of claim 1, wherein the graphical index employs color-coded indices to indicate the accuracy of the tracked spatial relationship relative to the actual spatial relationship.

7. The method of claim 1, wherein the graphical index numerically displays the quantified deviation to indicate the accuracy of the tracked spatial relationship relative to the actual spatial relationship.

8. The method of claim 1, wherein the visual representations include at least one three-dimensional model of the anatomical region.

9. A method for verifying an accuracy of a tracked spatial relationship between a robotic device and an anatomical region relative to an actual spatial relationship therebetween, comprising the steps of:
    tracking identifiers associated with first markers to determine a tracked spatial pose of a probe tip of a probe held by a robotic device, the spatial pose of the probe tip indicative of a pose of a robotic device based on a known geometric relationship between the probe tip and the robotic device;
    tracking identifiers associated with second markers to determine a tracked spatial pose of an anatomical region based on an array of anatomical checkpoints disposed on or in the anatomical region;
    mapping a tracked spatial proximity between the probe tip and the anatomical region based on the tracked spatial pose of the probe tip and the tracked spatial pose of the anatomical region at a selected checkpoint defined within the anatomical region;
    generating a graphical user interface based on the tracked spatial proximity and captured medical images;
    facilitating, by the robotic device, an actual contact of the probe tip with the anatomical region at one of the anatomical checkpoints facilitated by the manipulation of the articulated arm;
    receiving a verification request that is initiated by a user selection and received through the graphical user interface, the verification request being indicative of the actual contact between the probe tip and the anatomical region at the checkpoint;
    determining the accuracy of the tracked spatial relationship between the anatomical region and the robotic device based on any deviation between the tracked spatial proximity and the tracked actual contact as indicated by the user selection; and
    generating a graphical index within the graphical user interface indicative of the accuracy of the spatial registration.

10. The method of claim 9, wherein the tracked spatial relationship is based on information corresponding to the tracked spatial pose of the probe tip and the tracked spatial pose of the anatomical region.

11. The method of claim 9, wherein the tracked spatial proximity is graphically mapped to at least one medical image of the anatomical region to be displayed within the graphical user interface.

12. The method of claim 9, wherein views within the graphical user interface are automatically adjusted to facilitate visualization of the probe tip.

13. The method of claim 9, further comprising the step of quantifying the deviation between the tracked spatial proximity and the actual contact as indicated by the user selection.

14. The method of claim 9, wherein the graphical index is configured to indicate the accuracy of the tracked spatial relationship relative to the actual spatial relationship based on the quantified deviation using one or more of color-coded indices and numerical indices.

15. A system for verifying an accuracy of a tracked spatial relationship between a robotic device and an anatomical region relative to an actual spatial relationship therebetween, comprising:
    the robotic device;
    a probe coupled to the robotic device, the probe comprising a probe tip and at least one first detectable marker, the probe having a first known geometric relationship with the robotic device;
    at least one second detectable marker configured to be coupled to the anatomical region with a second known geometric relationship with at least one anatomical checkpoint disposed on or in the anatomical region;
    a detector configured to sense a position of the at least one first detectable marker to facilitate tracking of a tracked spatial pose of the probe tip, and to sense a position of the at least one second detectable marker to facilitate tracking of a tracked spatial pose of the anatomical region; and
    a computing device in communication with at least the detector, the computing device comprising an input device, a display device, a memory, and at least one controller, the controller configured to determine a tracked spatial proximity of the probe tip relative to the anatomical region based on the tracked spatial pose of the probe tip and the tracked spatial pose of the anatomical region, map the tracked spatial proximity between the probe tip and the anatomical region onto a visual representation of the anatomical region based on tracking information provided by the detector, receive a verification request through the input device that is indicative of an actual spatial proximity between the probe tip and the anatomical region at the checkpoint, quantify a deviation between the mapped spatial proximity and the actual spatial proximity in response to the verification request, and display a graphical index on the display device that is indicative of a degree of accuracy of the tracked spatial relationship between the robotic device and the anatomical region based on the quantified deviation.

16. The system of claim 15, wherein the graphical index employs color-coded indices to indicate the degree of accuracy of the tracked spatial relationship between the robotic device and the anatomical region.

17. The system of claim 15, wherein the graphical index numerically displays the quantified deviation to indicate the degree of accuracy of tracked spatial relationship between the robotic device and the anatomical region.

18. The system of claim 15, wherein the visual representation includes at least one medical image of the anatomical region that is at least temporarily stored within the memory of the computing device and viewable through the display device.

19. The system of claim 15, wherein the visual representation includes at least one three-dimensional model of the anatomical region.

20. The system of claim 15, wherein the controller is configured to generate a graphical user interface through the display device to facilitate interactions with the user, the graphical user interface including at least the graphical index.

21. The system of claim 20, wherein the controller is configured to automatically adjust views within the graphical user interface to facilitate visualization of the probe tip.

22. The system of claim 15, wherein the controller is configured to communicate with the robotic device which at least partially supports the probe, the controller being configured to selectively control a spatial pose of the probe tip by controlling the robotic device.

* * * * *